United States Patent [19]

Reynolds et al.

[11] 3,964,484

[45] June 22, 1976

[54] ANTICOAGULANT METERING DEVICE AND METHOD

[75] Inventors: Gordon S. Reynolds; A. Boyd Hansen, both of Bountiful, Utah

[73] Assignee: Sorenson Research Co., Inc., Salt Lake City, Utah

[22] Filed: Mar. 3, 1975

[21] Appl. No.: 555,008

[52] U.S. Cl. .............................. 128/276; 128/240
[51] Int. Cl.² ................. A61M 1/100; A61M 27/00
[58] Field of Search ........... 128/274, 276, 277, 278, 128/214 R, 240, 241; 137/88, 114

[56] References Cited
UNITED STATES PATENTS

| | | | |
|---|---|---|---|
| 2,629,399 | 2/1953 | Kulick | 128/240 X |
| 2,804,075 | 8/1957 | Borden | 128/277 |
| 3,335,727 | 8/1967 | Spoto | 128/276 |
| 3,769,982 | 11/1973 | Schulte | 128/350 V |
| 3,807,401 | 4/1974 | Riggle et al. | 128/277 |

*Primary Examiner*—Dalton L. Truluck
*Attorney, Agent, or Firm*—H. Ross Workman; J. Winslow Young

[57] ABSTRACT

An aspiration wand assembly having an associated metering valve for metering liquid anticoagulant to blood aspirated by the wand. The metering valve includes a flexible diaphragm normally obstructing conduit which transmits anticoagulant from a remote source to the tip of the aspiration wand. An orifice communicates the diaphragm with the interior of the aspiration wand so that various negative pressures in the wand correspondingly draw the diaphragm into any one of a plurality of positions away from the obstructing position.

11 Claims, 4 Drawing Figures

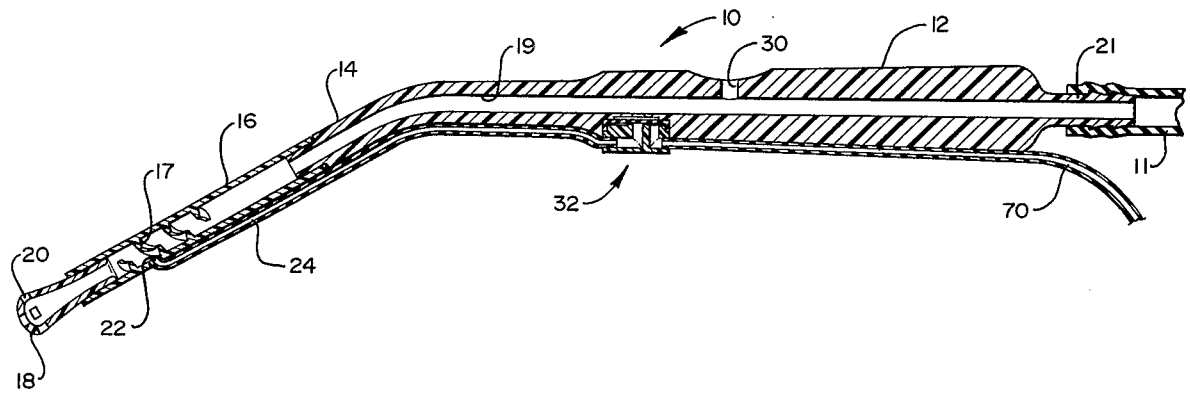
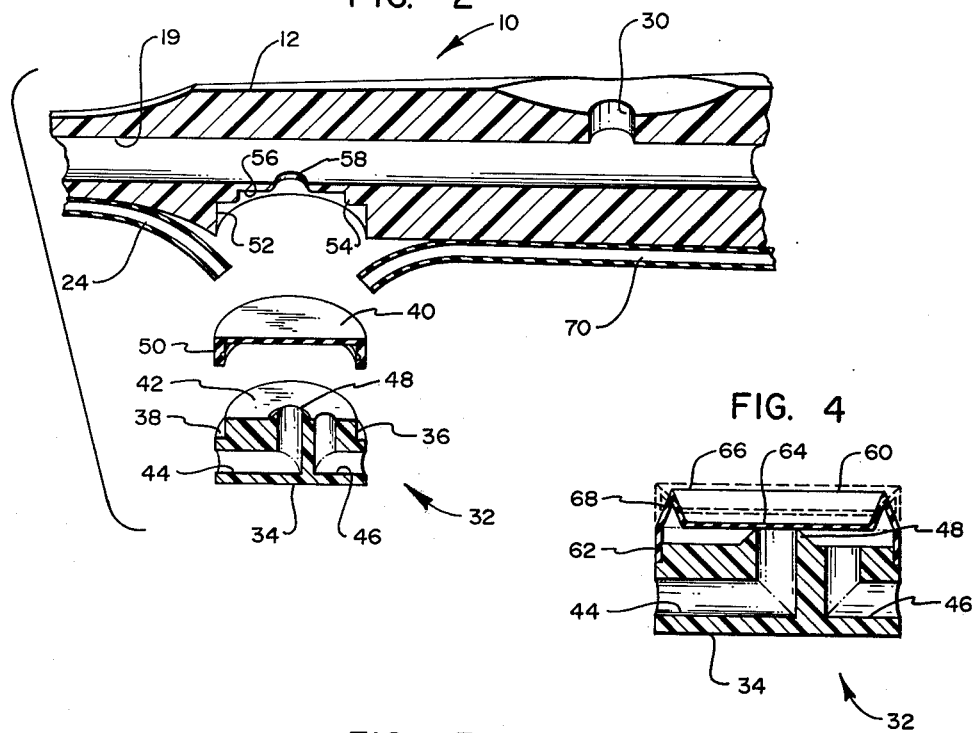
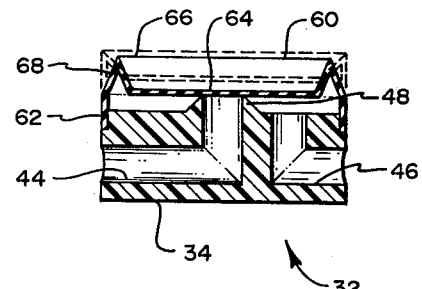
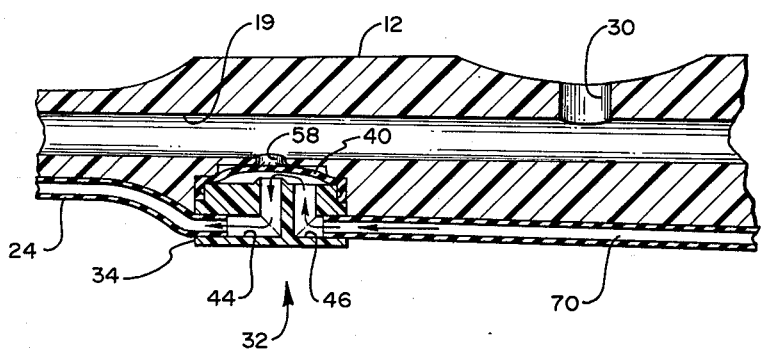

ANTICOAGULANT METERING DEVICE AND METHOD

BACKGROUND

1. Field of the Invention

The invention relates to aspiration of blood for autologous blood transfusion and more particularly to structure and method for metering anticoagulant to the aspirated blood.

2. The Prior Art

Intraoperative autotransfusion is increasingly recognized as providing an effective means of returning blood lossed at the operating site directly to the patient without the recognized complications and disadvantages of stored bank blood. It is recognized, however, that widespread autotransfusion has not been uniformly adopted heretofore in large part because of the inability to meter the appropriate amount of anticoagulant to the blood in the course of aspiration.

Historically, two primary techniques were used to control the coagulation of autologous blood. First, anticoagulant such as acid citrate or heparin have been introduced by "in line" drip directly into a collection reservoir. This method requires constant monitoring to assure proper anticoagulation and does not prevent clot formation in the vacuum line between the suction tip and the collection reservoir.

A second technique is referred to as systemic heparinization. According to this technique, anticoagulant is injected intravenously in sufficient amounts that all of the patient's blood is affected by the anticoagulant. While this method has proved satisfactory for selected kinds of peripheral vascular surgery, it has not been accepted in those patients in whom a significant amount of soft tissue dissection is anticipated or in patients suffering from multiple trauma. Further, systemic heparinization has made post-operative hemostasis much more difficult.

Most recently, efforts have been made to deliver anticoagulant to blood as the blood passes through a venturi in the handle of an aspiration wand. See, for example, U.S. Pat. No. 3,807,401 and the American Journal of Surgery, Volume 123, March 1972, page 257 et. seq.

The trauma involved in passing whole blood through a venturi has proved to be undesirably hemolytic. Furthermore, the complicated construction of such devices generally makes them too expensive to be disposable. Finally, special exterior valving structure is required to prevent retrograde flow of the anticoagulant from the suction wand at the conclusion of each aspiration.

It would therefore be a valuable contribution to the art to provide an improved aspiration wand with an anticoagulant metering device which forms an effective positive control on the volume of anticoagulant metered to aspirated blood in a facile and inexpensive manner.

BRIEF SUMMARY AND OBJECTS OF THE INVENTION

The present invention provides method and apparatus for metering anticoagulant to aspirated blood in response to pressure changes within an aspiration wand. Various negative pressures in the aspiration wand displace the flexible membrane away from an obstructing position across anticoagulant-transmitting conduit in an amount generally corresponding to the magnitude of the negative pressure. Anticoagulant in the conduit will thus be delivered only when the diaphragm is away from its obstructing position and the amount of flow is positively controlled by the diaphragm.

It is, therefore, a primary object of the present invention to provide improvements in metering anticoagulant to aspirated blood.

A more particular object of the present invention is to provide a novel metering valve cooperating with an aspiration wand assembly to deliver anticoagulant to the aspirant in a predetermined amount.

It is another principal object of the present invention to positively control the delivery of anticoagulant to aspirated blood.

One still further object of the present invention is to provide a flexible diaphragm which normally obstructs the flow path of anticoagulant but which responds to negative pressure in the aspiration wand to open the flow path in an amount corresponding to the magnitude of the negative pressure and for as long as the negative pressure exists.

Another valuable object of the present invention is to provide a metering valve which is simple in construction and can be easily adapted for use in a conventional disposable aspiration wand.

One still further object of the present invention is to provide method and apparatus for delivering anticoagulant into aspirated blood in predetermined amounts immediately after the blood has passed into the aspiration wand.

It is a further object of the present invention to provide a metering valve having a diaphragm which is resistant to material fatigue.

Another object of the present invention is to provide an improved aspiration wand assembly having a finger-actuated control port and a metering valve in open communication with the aspiration passageway in the aspiration wand, the metering valve being located so as to terminate the flow of anticoagulant when the control port is uncovered.

These and other objects and features of the present invention will become more fully apparent from the following description and appended claims taken in conjunction with the accompanying drawings.

BRIEF DESCRIPTION OF THE DRAWING

FIG. 1 is a longitudinal cross-sectional view of an aspiration wand assembly utilizing one preferred embodiment of the metering valve of the present invention;

FIG. 2 is an enlarged exploded cross-sectional view of the metering valve of FIG. 1, portions being broken away for ease of illustration;

FIG. 3 is an enlarged cross-sectional view of the metering valve of FIG. 2 in the assembled configuration, the diaphragm thereof being illustrated in the full open position; and FIG. 4 is a fragmentary cross-sectional view of another presently preferred metering valve embodiment, the full open position being illustrated in broken lines.

DETAILED DESCRIPTION OF THE PREFERRED EMBODIMENTS

The Structure

Reference is now made to the drawings wherein like parts are designated with like numerals throughout. Referring particularly to FIG. 1, an aspiration wand assembly generally designated 10 is illustrated. Conventionally, the aspiration wand 10 comprises a handle 12 and an integral probe 14. The probe 14 terminates in a rounded tip 18 having ports 20 therein. The handle 12, probe 14 and tip 18 define a continuous hollow passageway 19 transversing the entire length of the wand 10. The handle 12 has a rearwardly projecting male coupling 21 into which the conventional vacuum bloodline 11 is pressfit. Probe 14 also includes a cylindrical mixing chamber 16 located in close proximity to the tip 18. The mixing chamber 16 is, in the illustrated embodiment, a cylindrical extension of the probe 14 and is hollow to permit internal mixing of blood and anticoagulant and a subsequent transport of the anticoagulated blood to a receptacle (not shown). In FIG. 1, the mixing chamber 16 is shown to be press-fit onto both the probe 14 and the tip 18. If desired, the mixing chamber can be integral with the probe and/or the tip 18.

In the embodiment of FIG. 1, the mixing chamber 16 circumscribes a baffle 17 which provides for a mechanical mixing of blood aspirated through the port 20 with anticoagulant delivered through port 22. The baffle 17 provides a convoluted path, which accommodates thorough mixing but at the same time avoids dramatic pressure changes and cellular trauma which tends to hemolyze blood cells.

Presently it is preferred that the handle 12 be provided with a control port 30 which can be conveniently closed with a finger or thumb. When the control port 30 is closed, vacuum in the passageway 19 will develop suction at the tip 18. However, when the control port 30 is open, negligible vacuum will appear in the passageway 19 forward of the port 30. Anticoagulant is delivered to the passageway 19 interior of the wand 10 through the port 22 which is located in the forward end of the mixing chamber 16 near the tip 18. Conduit 24 is mounted in the port 22 and communicates the port 22 with the metering valve generally designated 32 and best illustrated in FIGS. 2 and 3.

Referring more particularly to FIGS. 2 and 3, the metering valve 32 includes a valve seat 34 which, in the illustrated embodiment is annular in configuration. The seat 34 is diametrally reduced at 36 to form an annular shoulder 38 adapted to receive a portion of the diaphragm 40 in a manner hereinafter to be more fully described. The seat terminates in a substantially planar upper surface 42.

The seat 34 is provided with two opposed generally axially aligned bores 44 and 46. The bore 44 emerges at the surface 42 at essentially the center thereof. Bore 46 emerges also at the surface 42 but radially spaced from the bore 44. In the illustrated preferred embodiment, the bore 44 emerges above the surface 42 through a conically configurated boss 48, the boss insuring a positive seal between the bore 44 and the bore 46 when the diaphragm 40 is in the appropriate obstructing position.

Diaphragm 40 is preferably formed of an elastic material with memory and presents a central disc-shaped portion and an integral downwardly directed skirt 50. The skirt 50 is dimensioned so as to fit snugly over the surface 42 and to abut the shoulder 38. In normal repose, the diaphragm 40 rests upon most of the surface 42 and impinges firmly over the boss 48 thereby obstructing bores 44 and 46.

The handle 12 is provided with a hollowed opening 52 corresponding in size and configuration with the exterior of the seat 34. Preferably, the hollow 52 is interrupted by an annular shoulder 54 situated so as to engage the external periphery of the diaphragm 40 when the diaphragm has been mounted upon the seat 34 and thereafter inserted into the hollow 52 as shown in FIG. 3. The base 56 of the hollow 52 is spaced above the seat 34 even when the seat 34 is in the full inserted position so as to allow the diaphragm 40 to lift away from the surface 42 and boss 48 as shown in FIG. 3.

It is further observed that the hollow 52 is provided with an orifice 58 which opens into the passageway 19. When the pressure is reduced in the passageway 19, such as during aspiration of blood, the diaphragm 40 will lift away from the surface 42 and boss 48 as shown in FIG. 3, the magnitude and duration of the lift being generally proportional to the negative pressure in the passageway 19. As shown in FIG. 3, the diaphragm is stretched at its central portion toward the orifice 58 in response to the reduced pressure in the passageway 19.

Another highly desirable and presently preferred diaphragm embodiment 60 is illustrated in FIG. 4. The diaphragm 60 includes an annular skirt 62 which, like the skirt 50, abuts the shoulder 38 of the seat 34. Diaphragm 60 differs principally in that the central portion 64 is recessed away from the upper surface 66 and is joined to the skirt 62 by tapered walls 68, the walls 68 gently biasing the central portion 64 into the position illustrated in FIG. 4. A principal advantage of this configuration becomes apparent when it is observed that negative pressure in the passageway 19 will lift the central portion 64 without significantly stretching the diaphragm material. Accordingly, failures due to material fatigue can be significantly reduced.

The valve seat 34, in the assembled position, provides for telescopic coupling of the conduit 24 with the bore 44. Also, the bore 46 is coupled with conduit 70 which communicates anticoagulant from a remote source to the metering valve 32.

The Method

The method of the present invention can best be understood by reference to FIGS. 1, 3 and 4. In initially preparing the wand assembly 10 for aspiration, the conduit 70 is connected to a source of anticoagulant such as heparin, acid citrate or the like. It has been found that the hydrostatic pressure exterted by the anticoagulant on the underside of the diaphragm 40 is in part a function of the height of the anticoagulant reservoir with respect to the wand assembly 10. Accordingly, it has been found desirable to maintain the reservoir of anticoagulant at approximately the same elevation as the surgical area in which the wand assembly 10 will be used. If desired, the hydrostatic pressure in conduit 70 can be increased by increasing the elevation of the anticoagulant reservoir so that a small trickle of anticoagulant occasionally passes beneath the diaphragm 40, through the conduit 24 and into the mixing chamber 16 so as to maintain a coating of anticoagulant along the conduit 19. Thus, the hydrostatic pressure on the underside of diaphragm 40 contributes to the sensitivity of the diaphragm to the pressure through orifice 58 as will now be more fully described.

To aspirate blood with the wand 10, the operator, generally a surgeon or his assistant, activates a vacuum source (not shown) to impose a vacuum in line 11 and thereafter inserts the tip 18 into blood which accumulates during surgery. If the control port 30 remains uncovered, no blood will be aspirated through the tip 18 and accordingly no anticoagulant will be delivered at the mixing chamber 16. Because the metering valve 32 is located between the tip 18 and the control port 30, the orifice 58 is not subjected to significant changes in pressure unless the control port 30 is covered.

When the control port 30 is covered, the vacuum will be imposed through the length of the passageway 19 thereby aspirating blood through the ports 20. It is also observed that the negative pressure in line 19 will be communicated through the orifice 58 to lift the diaphragm toward the position illustrated in FIG. 3. The actual quantity of anticoagulant delivered will depend upon the degree of opening of the diaphragm and the hydrostatic pressure of the anticoagulant. Anticoagulant in the conduit 70 and 24 will then be permitted to pass through the valve seat 32 as represented by the arrows in FIG. 3. Thus, a metered amount of anticoagulant will be delivered to the aspirated blood immediately after it passes through the ports 20. It is pointed out that even if the magnitude of the vacuum in line 19 is reduced so that blood is aspirated only slowly, a reduced amount of anticoagulant will be made available because the diaphragm will not be lifted the full distance into the hollow 52.

Similarly, where diaphragm 60 is used, the negative pressure in the passageway 19 will be communicated through the orifice 58 to lift the diaphragm 60 from the solid line toward the broken line position thereby permitting the flow anticoagulant through the valve seat 34.

While the control port 30 has proved highly desirable to give positive control of the metering valve 32 whether or not the tip 18 is immersed, the port 30 could be omitted so that the operation of the metering valve 32 is more dependent upon the prescence of liquid at the tip 18.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced with their scope.

What is claimed and desired to be secured by United States Letters Patent is:

1. A blood aspiration wand assembly for metering anticoagulant to aspirated blood comprising:
   an elongated wand comprising a perforated suction tip and an interior passageway which is selectively evacuated to accommodate aspiration of blood at the tip and displacement of the blood through the passageway toward a receiving container;
   conduit means for carrying anticoagulant from a source to the passageway;
   valve means interposed in the conduit means; and
   means communicating the passageway with the valve means, the valve means comprising means displaceable between open and closed positions responsive to changes in pressure in the passageway communicated to the valve means through the communicating means for metering the quantity of anticoagulant passing through the conduit.

2. An aspiration wand assembly for metering a liquid to the aspirant comprising:
   an elongated wand comprising a perforated suction tip and an interior passageway communicating the suction tip with the vacuum source;
   a conduit for conducting liquid from a remote source to the passageway of the wand; and
   a metering valve interposed in the conduit, the metering valve comprising a valve seat containing a portion of the conduit, a flexible diaphragm adjacent the valve seat and selectively interposed across the conduit path, an orifice communicating the diaphragm with the interior passageway of the wand, the diaphragm responding to changes in pressure in the passageway by moving between any one of a plurality of positions to meter the amount of liquid passing through the conduit.

3. An aspiration wand assembly as defined in claim 2 wherein said valve seat comprises an orifice exposing the conduit path and wherein said diaphragm comprises a rubber layer normally resting upon and occluding the orifice, the rubber layer being selectively lifted away from the orifice due to negative pressure in the passageway in the wand.

4. An aspiration wand assembly as defined in claim 3 wherein the orifice in the valve seat is surrounded by an annular boss which tapers to a sharp edge to facilitate fluid-type seating of the diaphragm.

5. An aspiration wand assembly as defined in claim 2 wherein the valve seat comprises an initially separate insert configurated to mate with a portion of the elongated wand, the periphery of the diaphragm being secured between the insert and the wand.

6. An aspiration wand assembly as defined in claim 2 wherein the diaphragm comprises an essentially planar surface and an angularly-projecting skirt to facilitate attachment of the diaphragm to the wand, the planar surface stretching toward an arcuate configuration in response to negative pressure in the passageway to permit liquid to flow through the conduit.

7. An aspiration wand assembly as defined in claim 2 wherein the diaphragm comprises an inwardly recessed central portion, a concentric skirt projecting away from the central portion, and means between the skirt and the recessed central portion for biasing the central portion against the seat, the central portion compressing at least part of the biasing means in response to negative pressure in the passageway to permit liquid to flow through the conduit.

8. A method of metering anticoagulant to blood aspirated by an aspiration wand, comprising the steps of:
   selectively evacuating the aspiration wand to create suction at the tip thereof;
   filling a conduit with anticoagulant, the conduit merging the anticoagulant flow path with the aspirant flow path near the tip of the wand;
   interposing a metering valve in the anticoagulant flow path, the metering valve comprising flow control means;
   communicating the pressure in the aspirant flow path to the metering valve; and
   displacing the flow control means from a closed position toward an open position in response to reduced pressure in the aspiration wand.

9. A method as defined in claim 8 wherein said evacuating step comprises covering an actuation port.

10. A method as defined in claim 8 wherein said displacing step comprises sensing pressure changes in the aspiration wand through an orifice communicating the flow control means with the aspirant flow path.

11. A method as defined in claim 8 further comprising adjusting the hydrostatic pressure of the anticoagulant in the conduit upstream from the metering valve to contribute to the sensitivity of the flow control means.

* * * * *